US009771323B2

(12) United States Patent
Sunilkumar et al.

(10) Patent No.: US 9,771,323 B2
(45) Date of Patent: Sep. 26, 2017

(54) BETA-CRYPTOXANTHIN FROM PLANT SOURCE AND A PROCESS FOR ITS PREPARATION

(71) Applicant: OMNIACTIVE HEALTH TECHNOLOGIES LIMITED, Mumbai (IN)

(72) Inventors: Thattaruparambil Krishna Das Sunilkumar, Pune (IN); Madapura Lingappiah Shankaranarayana, Mysore (IN); Padinjarevattom Abdulkadir Sherena, Pune (IN); Jeyakodi Shankarnarayanan, Thane (IN)

(73) Assignee: OMNIACTIVE HEALTH TECHNOLOGIES LIMITED, Mumbai (IN)

( * ) Notice: Subject to any disclaimer, the term of this patent is extended or adjusted under 35 U.S.C. 154(b) by 124 days.

(21) Appl. No.: 14/763,470

(22) PCT Filed: Jan. 23, 2014

(86) PCT No.: PCT/IB2014/000478
§ 371 (c)(1),
(2) Date: Jul. 24, 2015

(87) PCT Pub. No.: WO2014/115037
PCT Pub. Date: Jul. 31, 2014

(65) Prior Publication Data
US 2015/0361040 A1  Dec. 17, 2015

(30) Foreign Application Priority Data

Jan. 24, 2013 (IN) .......................... 214/MUM/2013

(51) Int. Cl.
| A61K 36/00 | (2006.01) |
| C07C 403/02 | (2006.01) |
| A61K 31/045 | (2006.01) |
| C07C 403/24 | (2006.01) |
| C09B 61/00 | (2006.01) |
| B01D 15/42 | (2006.01) |
| A23L 5/44 | (2016.01) |
| A23L 33/105 | (2016.01) |

(52) U.S. Cl.
CPC ............. *C07C 403/02* (2013.01); *A23L 5/44* (2016.08); *A23L 33/105* (2016.08); *A61K 31/045* (2013.01); *B01D 15/426* (2013.01); *C07C 403/24* (2013.01); *C09B 61/00* (2013.01); *A23V 2002/00* (2013.01); *C07C 2601/16* (2017.05)

(58) Field of Classification Search
None
See application file for complete search history.

(56) References Cited

U.S. PATENT DOCUMENTS 7,115,786 B2  10/2006  Khachik
8,148,431 B2   4/2012  Yamaguchi 2006/0106115 A1   5/2006  Yamaguchi
2006/0121557 A1   6/2006  Hoshino et al.
2007/0116818 A1   5/2007  Takahashi et al.
2008/0070980 A1   3/2008  Eichinger et al.
2008/0124755 A1   5/2008  Louie et al.
2009/0093015 A1   4/2009  Louie et al.
2009/0258111 A1  10/2009  Takayanagi et al.
2009/0311761 A1  12/2009  Khachik et al.
2012/0053247 A1   3/2012  Showalter et al.

FOREIGN PATENT DOCUMENTS

| CN | 1953669 A | 4/2007 |
| CN | 101330839 A | 12/2008 |
| CN | 102 219 721 A | 10/2011 |
| EP | 1 825 858 A1 | 8/2007 |
| JP | 2000136181 A | 5/2000 |
| WO | WO 02/060865 A1 | 8/2002 |
| WO | WO 2006/114974 A1 | 11/2006 |

OTHER PUBLICATIONS

Barreto et al, Bioactive compounds and free radical scavenger activity in ingredients prepared from the waste of the cashew-apple nut industry. Compostos bioativos em sub-produtos da castanha de caju. Alimentos e Nutricao (2007), vol. 18, No. 2, pp. 207-213.*
Rodriguez, G. A. "Extraction, Isolation, and Purification of Carotenoids," *Current Protocols in Food Analytical Chemistry*, F2.1.1-F2.1.8, Wiley, United States (2001), 9 pages.
Search Report and Written Opinion for Application No. 11201505759R, Intellectual Property Office of Singapore, Singapore, mailed on Mar. 17, 2016, 24 pages.
Notification of the First Office Action, State Intellectual Property Office of the People's Republic of China, Chinese Application No. 201480014666.0, Dated Jul. 4, 2016, 23 pages (English Translation Included).
Bieri, J.G., et al., "Determination of Individual Carotenoids in Human Plasma by High Performance Liquid Chromatography," *Journal of Liquid Chromatography* 8(3):473-484, Marcel Dekker, Inc., United States (1985).
Breithaupt, D.E. and Bamedi, A., "Carotenoid esters in vegetables and fruits: A screening with emphasis on β-cryptoxanthin esters," *Journal of Agriculture and Food Chemistry* 49(4):2064-2070, American Chemical Society, United States (2001).

(Continued)

*Primary Examiner* — Qiuwen Mi
(74) *Attorney, Agent, or Firm* — Sterne, Kessler, Goldstein & Fox PLLC

(57) ABSTRACT

The present invention provides beta-cryptoxanthin crystals from plant source and a process for its preparation. The present invention particularly relates to a process for the preparation of high purity beta-cryptoxanthin crystals comprising at least about 10% by weight total xanthophylls, of which at least about 75% by weight is trans-beta-cryptoxanthin and the remaining including beta-carotene, and trace amounts of trans-capsanthin and other carotenoids derived from the plant source, including *capsicum* fruits. The production of beta-cryptoxanthin crystals with high content of trans-beta-cryptoxanthin makes it ideal and suitable for use as a provitamin A source material and also has potential effects on improving bone health and inhibiting bone resorption.

19 Claims, 4 Drawing Sheets

(56) References Cited

OTHER PUBLICATIONS

Breithaupt, D.E., et al., "Plasma response to a single dose of dietary β-cryptoxanthin ester from papaya (*Carica papaya* L.) or non-esterified β-cryptoxanthin in adult human subjects: a comparative study," *British Journal of Nutrition* 90(4):795-801, Published on behalf of the Nutrition Society by CABI Publishing, England (2003).

Burri, B.J., et al.,"β-cryptoxanthin- and α-carotene-rich foods have greater apparent bioavailability than β-carotene-rich foods in Western diets," *British Journal of Nutrition* 105(2):212-219, Published on behalf of the Nutrition Society by CABI Publishing, England (2011).

Cerhan, J.R., et al., "Antioxidant Micronutrients and Risk of Rheumatoid Arthritis in a Cohort of Older Women," *American Journal of Epidemiology* 157(4):345-354, Johns Hopkins Bloomberg School of Public Health, United States (2003).

Craft, N.E., et al., "Carotenoids, tocopherol and retinol concentrations in elderly human brain," *The Journal of Nutrition, Health and Aging* 8(3):156-162, Springer Pub. Co., France (2004).

Irwig, M.S., et al., "Frequent intake of tropical fruits that are rich in β-cryptoxanthin is associated with higher plasma β-cryptoxanthin concentrations in Costa Rican adolescents," *The Journal of Nutrition* 132:3161-3167, American Society for Nutritional Science, United States (2002).

Khachik, F., et al., "Partial synthesis of (3R,6 'R)-α-cryptoxanthin and (3R)-β-cryptoxanthin from (3R,3'R,6 'R)-lutein," *Journal of Natural Products* 70(2):220-226, American Chemical Society and American Society of Pharmacognosy, United States (2007).

Pattison, D.J., et al., "Dietary β-cryptoxanthin and inflammatory polyarthritis: results from a population-based prospective study," *The American Journal of Clinical Nutrition* 82:451-455, American Society of Clinical Nutrition, United States (2005).

Pèrez-Gálvez, A., et al., "Incorporation of carotenoids from paprika oleoresin into human chylomicrons," *British Journal of Nutrition* 89(6):787-793, Published on behalf of the Nutrition Society by CABI Publishing, England (2003).

Serrato-Joya, O., et al., "Production of β-Cryptoxanthin, a Provitamin-A Precursor by *Flavobacterium Lutescens,*" *Journal of Food Science* 71(6):E314-E319, Institute of Food Technologists, United States (2006).

Shirakura, Y., et al., "Reducing effect of β-cryptoxanthin extracted from Satsuma mandarin on human body fat," *Carotenoid Science* 12:Abstract, Abstracts of the Papers presented at the 15$^{th}$ International Symposium on Carotenoids, Okinawa, Japan, Jun. 22-27, 2 pages (2008).

Takayanangi, K. and Mukai, K., "β-cryptoxanthin (β-CRX) and Satsuma mandarin: Industrial production and health promoting benefits," *Carotenoid Science* 12:Abstract, Abstracts of the Papers presented at the 15th International Symposium on Carotenoids, Okinawa, Japan, Jun. 22-27, 2 pages (2008).

Uchiyama, S. and Yamaguchi, M., "Anabolic Effect of Marine Alga *Sargassum horneri* Extract on Bone Components in the Femoral-diaphyseal and -metaphyseal Tissues of Young and Aged Rats in Vivo," *Journal of Health Science* 48(4):325-330, David Publishing Company, United States (2002).

Uchiyama, S., et al., Anabolic effect of β-cryptoxanthin on bone components in the femoral tissues of aged rats in Vivo and in Vitro, *Journal of Health Science* 50(5):491-496, David Publishing Company, United States (2004).

Uchiyama, S. and Yamaguchi, M., "Oral Administration of β-Cryptoxanthin Prevents Bone Loss in Streptozotocin-Diabetic Rats in Vivo," *Biological and Pharmaceutical Bulletin* 28(9):1766-1769, Pharmaceutical Society of Japan, Japan (2005).

Uchiyama, S. and Yamaguchi, M., "Oral administration of β-cryptoxanthin prevents bone loss in ovariectomized rats," *International Journal of Molecular Medicine* 17:15-20, Spandidos Publications, England (2006).

Wingerath, T., et al., "β-cryptoxanthin selectively increases in human chylomicrons upon ingestion of tangerine concentrate rich in β-cryptoxanthin esters," *Archives of Biochemistry and Biophysics* 324(2):385-390, Academic Press, United States (1995).

Yamaguchi, M., et al., "Effect of marine algae extract on bone calcification in the femoral-metaphysical tissues of rats: Anabolic effect of *Sargassum horneri,*" *Journal of Health Science* 47(6):533-538, David Publishing Company, United States (2001).

Yamaguchi, M. and Uchiyama, S., "Effect of carotenoid on calcium content and alkaline phosphatase activity in rat femoral tissues in Vitro: The unique anabolic effect of β-cryptoxanthin," *Biological and Pharmaceutical Bulletin* 26(8):1188-1191, Pharmaceutical Society of Japan, Japan (2003).

Yamaguchi, M. and Uchiyama, S., "β-cryptoxanthin stimulates bone formation and inhibits bone resorption in tissue culture in vitro," *Molecular and Cellular Biochemistry* 258(1-2):137-144, Kluwer Academic, Netherlands (2004).

Yamaguchi, M., et al., "Prolonged intake of juice (*Citrus unshiu*) reinforced with β-crypthoxanthin has an effect on circulating bone biochemical markers in normal individuals," *Journal of Health Science* 50(6):619-624, David Publishing Company, United States (2004).

Yamaguchi, M., et al., "Relationship between serum β-cryptoxanthin and circulating bone metabolic markers in healthy individuals with the intake of juice (*Citrus unshiu*) containing β-cryptoxanthin," *Journal of Health Science* 51(6):738-743, David Publishing Company, United States (2005).

Yamaguchi, M., et al., "Effect of β-cryptoxanthin on circulating bone biomarkers intake of juice (*Citrus unshiu*) supplemented with β-cryptoxanthin has effect in menopausal women," *Journal of Health Science* 52(6):758-768, David Publishing Company, United States (2006).

Yamaguchi, M., et al., "Oral Administration in Combination with Zinc Enhances β-cryptoxanthin-Induced Anabolic Effects on Bone Components in the Femoral Tissues of Rats in Vivo," *Biological and Pharmaceutical Bulletin* 29(2):371-374 Pharmaceutical Society of Japan, Japan (2006).

Yamaguchi, M., "β-Cryptoxanthin and bone metabolism: The preventive role in osteoporosis," *Journal of Health Science* 54(4):356-369, David Publishing Company, United States (2008).

Yamaguchi, M., "Role of carotenoid β-cryptoxanthin in bone homeostasis," *Journal of Biomedical Science* 19(1):36, BioMed Central, England, 13 pages (2012).

Yuan, J-M., et al., "Dietary cryptoxanthin and reduced risk of lung cancer: the Singapore Chinese health study," *Cancer Epidemiology, Biomarkers & Prevention* 12(9):890-898, American Association for Cancer Research, United States (2003).

English language Abstract of Chinese Patent Publication No. 102219721 A, European Patent Office, espacenet database—Worldwide, (2011) (listed as document FP1 on the accompanying form PTO/SB/08A).

International Preliminary Report on Patentability for International Application No. PCT/IB2014/000478, European Patent Office, Netherlands, mailed on Jul. 28, 2015, 9 pages.

International Search Report for International Application No. PCT/IB2014/000478, European Patent Office, Netherlands, mailed on Oct. 13, 2014, 6 pages.

\* cited by examiner

BETA-CRYPTOXANTHIN FROM PLANT SOURCE AND A PROCESS FOR ITS PREPARATION

BACKGROUND OF THE INVENTION

Field of the Invention

The present invention relates to natural beta-cryptoxanthin concentrates of high purity and a process for its preparation. More particularly, the present invention provides beta-cryptoxanthin concentrates containing about 10-80% by weight total xanthophylls (total carotenoids) of which the trans-beta-cryptoxanthin content is about 75-98% by weight and the remaining including zeaxanthin, trans-capsanthin, beta-carotene and trace amounts of other carotenoids. The concentrates are particularly useful as dietary supplements for nutrition and health promoting benefits.

The invention also provides a process for the preparation of the beta-cryptoxanthin concentrate from plant oleoresin, especially from *Capsicum* oleoresin. The process includes the steps of admixing the oleoresin with alcohol solvents, saponifying the xanthophyll esters, washing and purifying by eluting the crude xanthophyll viscous concentrate on a silica gel column and purifying further by washings to obtain high purity trans-beta cryptoxanthin enriched concentrate crystals.

Background

Carotenoids represent one of the most widespread groups of naturally occurring fat-soluble pigments imparting yellow, red and orange color in plants as well as in animals. These absorb light in the 400-500 nm region of the visible spectrum and have a common chemical feature, a polyisoprenoid structure, a long conjugated chain of double bonds in the central portion of the molecule and near symmetry around the central double bond. The basic structure can be modified in a number of ways such as by cyclization of the end groups and by introduction of oxygen functions (O—H, C=O) to yield a large family of more than 600 compounds, exclusive of cis- and trans-isomers. Mammalian species do not synthesize carotenoids, and therefore they have to be obtained from dietary sources such as fruits and vegetables and/or dietary supplements.

Carotenoids are classified into hydrocarbon carotenoids, with lycopene and beta-carotene being the important members, and oxycarotenoids (xanthophylls), to which belongs mono-hydroxylated beta-cryptoxanthin while lutein, zeaxanthin and astaxanthin are dihydroxylated. The biosynthetic pathway of enzymatic hydroxylation of symmetrical beta-carotene (beta, beta-carotene) leads to the formation of beta-cryptoxanthin (beta,beta-caroten-3-ol) whereas the same reaction starting from asymmetric alpha-carotene (beta, epsilon-carotene) gives rise to two reaction products, namely: alpha-cryptoxanthin (beta,epsilon-caroten-3'-ol) and zeinoxanthin (beta, epsilon-caroten-3-ol). Often, because of the spectral structural similarities between alpha-cryptoxanthin and zeinoxanthin, their identification is difficult and misleading unless chemical reactions are carried out such as methylation or base catalyzed isomerization. Further, the chemical structures of these (see FIG. 1) are also given wrongly in many publications.

Among the 20 carotenoids detected in mammalian plasma and tissues, beta-cryptoxanthin is one of the major carotenoids detected along with lutein, zeaxanthin, beta-carotene and lycopene, together accounting for nearly 90% of the carotenoids. (J. G. Bieri, E. D. Brown and J. C. Smith, Determination of individual carotenoids in human plasma by HPLC, J. Liq. Chromatogr. 8, 473-484, 1985). Beta-cryptoxanthin, a provitamin A, plays an important role in the diet, finally converting in the human body into an active form of vitamin A (retinol), a nutrient important for vision, immune function, and skin and bone health. Beta-cryptoxanthin has about one half the vitamin A activity of the major vitamin precursor, beta-carotene. In addition, beta-cryptoxanthin acts as an antioxidant in the body. Wingerath et. al. (1995) studied the uptake of beta-cryptoxanthin after ingestion of tangerine juice concentrate rich in beta-cryptoxanthin esters. Beta-cryptoxanthin in substantial amounts was detected both in human chylomicrons and in serum (T. Wingerath, W. Stahl and H. Sies, Beta-cryptoxanthin selectively increases in human chylomicrons upon ingestion of tangerine concentrate rich in beta-cryptoxanthin, Arch. Biochem. and Biophys., 324, 385-390, 1995). The bioavailability of the carotenoids from paprika oleoresin has shown the presence of beta-carotene and beta-cryptoxanthin in higher amounts in chylomicrons compared to zeaxanthin among the volunteers (A. Perez-Galvez, H. D. Martin, H. Sies and W. Stahl, Incorporation of carotenoids from paprika oleoresin into human chylomicrons, J. Nutrition, 89, 787-793, 2003). Burri et al. (2011) have reported that beta-cryptoxanthin bioavailability seems to be 7-fold greater than beta-carotene under similar conditions. Therefore, beta-cryptoxanthin can likely be a valuable and potential source of vitamin A, which needs further study and confirmation (B. J. Burri, S. Jasmine, T. Chang and T. R. Neidlinger, Beta-cryptoxanthin- and alpha-carotene-rich foods have greater apparent bioavailability than beta-carotene-rich foods in Western diets, Brit. J. Nutrition, 105, 212-219, 2011).

Unlike other carotenoids, beta-cryptoxanthin is not found in most fruits or vegetables but is present in certain specific foods such as *capsicum* species, citrus fruits, mango, *papaya*, and pumpkin in small amounts, e.g., at about 10-20 mg/100 g in these fruits and vegetables. Mostly, beta-cryptoxanthin is present in an ester form in paprika and mandarin fruits. Breithaupt and Bamedi (2001) have analyzed a large number of fruits and vegetables and reported the beta-cryptoxanthin ester concentration levels. The highest ester concentrations were found in red chilies (17.1 mg/100 g), tangerine and oranges (Carotenoid esters in vegetables and fruits: A screening with emphasis on beta-cryptoxanthin esters, J. Agric. 49, 2064-2070, 2001). Later, Breithaupt et al., in a randomized, single-blind crossover study using a single dose of esterified or non-esterified beta-cryptoxanthin in equal amounts found no difference in the resulting plasma response among 12 volunteers suggesting a comparable bioavailability. (D. E. Breithaupt, P. Weller, M. Wolters and A. Hahn, Plasma response to a single dose of dietary Beta-cryptoxanthin ester from *papaya, Carica papaya*, or non-esterified beta-cryptoxanthin in adult human subjects: a comparative study, Brit. J. Nutr. 90, 795-801, 2003). Takayanagi and Mukai (2009) developed bioavailable composition of beta-cryptoxanthin derived from citrus unshiu Marc by using an enzyme process and in combination with dietary fiber (U.S. Pat. Appl. Pub. No. 2009/0258111, Highly bioavailable oral administration composition of cryptoxanthin).

In most of the Western countries and Japan, the dietary source of beta-cryptoxanthin comes from citrus fruits and their products and consequently the plasma beta-cryptoxanthin levels can be considered as a good index of the amount of fruit consumption. Similarly, in fruits such as *papaya* widely consumed in many tropical countries (e.g., Latin America), a high correlation of plasma beta-cryptoxanthin has been reported (M. S. Irwig, A. El-Sohemy, A. Baylin, N. Rifai and H. Campos, Frequent intake of tropical fruits that are rich in beta-cryptoxanthin is associated with higher plasma beta-cryptoxanthin concentrations in Costa Rican adolescents, J. Nutr. 132, 3161-3167, 2002).

The water soluble extract of marine algae extract, specifically *Sargassum horneri* showed an anabolic effect on bone calcification in the femoral-metaphysical tissue of young and old rats in vivo and in vitro, suggesting its role in the prevention of osteoporosis (Yamaguchi et al., Effect of marine algae extract on bone calcification in the femoral-metaphysical tissues of rats: Anabolic effect of *Sargassum horneri*, J. Health Sci., 47, 533-538, 2001; Uchiyama and Yamaguchi, Anabolic effect of marine alga *Sargassum horneri*, Effect on bone components in the femoral-diaphyseal and -metaphyseal tissues of young and old rats in vivo, J. Health Sci. 48, 325-330, 2002). Later, in a study of the effects of the various carotenoids, beta-cryptoxanthin showed a significant increase in calcium content and alkaline phosphatase activity in the femoral-diaphyseal (cortical bone) and femoral-metaphyseal (trabecular bone) tissues, suggesting that beta-cryptoxanthin possesses a unique anabolic effect on bone calcification in vitro (Yamaguchi and Uchiyama, Effect of carotenoid on calcium content and alkaline phosphatase activity in rat femoral tissues in vitro: The unique anabolic effect of beta-cryptoxanthin, Biol. Pharma. Bull. 26, 1188-1191, 2003). In another study, the DNA content in bone tissues was found to increase significantly and showed inhibitory effect on bone-resorbing factors-induced bone resorption in rat bone tissues in vitro (Uchiyama et al., Anabolic effect of beta-cryptoxanthin on bone components in the femoral tissues of aged rats in vivo and in vitro, J. Health Sci. 50, 491-496, 2004; Yamaguchi and Uchiyama, Beta-cryptoxanthin stimulates bone formation and inhibits bone resorption in tissue culture in vitro, Mol. Cell. Biochem. 258, 137-144, 2004).

Thus, beta-cryptoxanthin has a potential role and effect in maintaining bone health and preventing osteoporosis. The various studies carried out by Yamaguchi et al. (2004, 2005, 2006 and 2008), have shown that regular daily intake of Satsuma mandarin juice (*Citrus unshiu*) and/or supplemented with beta-cryptoxanthin (3-6 mg or more/day) has beneficial effects such as preventive effect on bone loss over age, stimulatory effect on bone formation and an inhibitory effect on bone re-absorption in normal and healthy individuals and in menopausal women (Prolonged intake of juice, *Citrus unshiu*, reinforced with beta-cryptoxanthin has an effect on circulating bone biomarkers in normal individuals, J. Health Sci., 50, 619-624, 2004; Relationship between serum beta-cryptoxanthin and circulating bone metabolic markers in healthy individuals with the intake of juice (*Citrus unshiu*) containing beta-cryptoxanthin. J. Health Sci., 51, 738-743, 2005; Effect of beta-cryptoxanthin on circulating bone biomarkers intake of juice (*Citrus unshiu*) supplemented with beta-cryptoxanthin has effect in menopausal women, J. Health Sci., 52, 758-768, 2006; Beta-Cryptoxanthin and bone metabolism: The prevention role in osteoporosis, J. Health Sci., 54, 356-369, 2008). Uchiyama and Yamaguchi (2005 & 2006) reported that oral administration of beta-cryptoxanthin isolated from Satsuma mandarin had a preventive effect in bone loss in streptozotocin (diabetic) and ovariectomized rats in vivo studies (Oral administration of beta-cryptoxanthin prevents bone loss in streptozotocin rats in vivo, Biol. Pharm. Bull. 28, 1766-1769, 2005; Oral administration of beta-cryptoxanthin prevents bone loss in ovariectomized rats, Int. J. Mol. Med. 17, 15-20, 2006). EP Application No. 058060229, Publn. 2007/35 (published as EP Publn. EP1825858) refers to a composition comprising beta-cryptoxanthin and zinc for promoting osteogenesis, increasing bone mineral content, thereby preventing bone diseases such as osteoarthritis. (M. Yamaguchi, Composition for promoting osteogenesis and increasing bone mineral content). U.S. Pat. No. 8,148,431 B2, Apr. 3, 2012, confirm that beta-cryptoxanthin has an osteogenesis promoting effect, a bone-resorption inhibiting effect and therapeutic effect on bone diseases (M. Yamaguchi, Osteogenesis promoter containing beta-cryptoxanthin as the active ingredient).

Generally, the different bone and joint disorders such as osteoporosis, osteoarthritis and rheumatoid arthritis are common among the elderly people and cause a major health problem resulting in bone fracture. With ageing there is a decrease in bone mass and an increase in bone resorption due to various dietary reasons. In recent publications, Yamaguchi has reviewed the recent advances concerning the role of beta-cryptoxanthin in the regulation of bone homeostasis and in the prevention of osteoporosis, especially the cellular and molecular mechanisms by which beta-cryptoxanthin stimulates osteoblastic bone formation and inhibits osteoclastic bone resorption (Beta-cryptoxanthin and bone metabolism: The preventive role in osteoporosis, J. Health Sci., 54, 356-369, 2008; Role of carotenoid beta-cryptoxanthin in bone homeostasis, J. Biomed. Sci., 19, 1-13, 2012).

High levels of dietary intake of beta-cryptoxanthin were found to be associated with reduced risk of lung cancer among the smoking population, thereby suggesting the xanthophylls as a chemo-preventive agent for lung cancer (Yuan et al., Dietary cryptoxanthin and reduced risk of lung cancer: the Singapore Chinese health study, Cancer Epidemiol. Biomarkers Prev. 12, 890-898, 2003). Craft et al. (2004) found beta-cryptoxanthin in the frontal cortex of brain which is considered to be associated with Alzheimer's disease, however explained no exact role for beta-cryptoxanthin (N. E. Craft, T. B. Haitema, K. M. Garnett, K. A. Fitch and C. K. Dorey, Carotenoids, tocopherol and retinol concentrations in elderly human brain, J. Nutr. Health Ageing, 8, 156-162, 2004). A high plasma level of beta-cryptoxanthin has been linked to a protective effect against rheumatoid arthritis. Pattison et al. (2005) attributed the incidence of inflammatory arthritis among 88 subjects to the low level of dietary intake of beta-cryptoxanthin (D. J. Pattison, D. P. Symmons, M. Lunt, A. Welch, S. A. Bingham, N. E. Day and A. J. Silman, Dietary beta-cryptoxanthin and inflammatory polyarthritis: results from a population based prospective study, Am. J. Clin. Nutri. 82,451-455, 2005). U.S. Pat. Appl. Pub. No. 2008/0070980 describes a method of use of beta-cryptoxanthin and its esters in the manufacture of a composition for providing increased protein formation and/or prevention of loss of proteins in human and animals, resulting in enhanced performance in sports and workout activities (E. Anne, G. Resina, W. Karin and W. Adrian, Use of beta-cryptoxanthin, Mar. 20, 2008). In a recent U.S. Patent Application entitled "Method of improving cardiovascular health," there is a finding that a nutritional supplement containing purified beta-cryptoxanthin (0.1 to 20 mg/day) is effective in lowering high blood pressure and also in maintaining a healthy blood pressure and cardiovascular health. However, the beta-cryptoxanthin used is purified by analytical HPLC from a mixture of alpha-cryptoxanthin, anhydroluteins, zeaxanthin, and other impurities (U.S. Pat. Appl. Pub. No. 2012/0053247, Publn. 1 Mar. 2012, H. Showalter, Z. Defretas and L. Mortensen).

In view of the increasing research interest in the various health benefits of beta-cryptoxanthin, there have been several approaches to commercially produce this carotenoid (1) from natural sources as extracts rich in beta-cryptoxanthin, (2) by biotechnology routes and (3) by total- and semi-synthesis. The various clinical studies have used either synthetic beta-cryptoxanthin or natural fruit extracts rich in beta-cryptoxanthin.

Natural Source Extracts

Yamaguchi (2006) referred to a method for separating beta-cryptoxanthin from Satsuma orange by extracting the pigment using hydrolyzation followed by silica gel column chromatography. The beta-cryptoxanthin fraction was further purified by octadecyl silicate silica to obtain 95% beta-cryptoxanthin (M. Yamaguchi, Osteogenesis promoter containing beta-cryptoxanthin as an active ingredient, U.S. Pat. Appl. Pub. No. 2006/0106115, published 18 May 2006). Takahashi and Inada (2007) have prepared Persimmon extract from pulp/juice and skin by solvent extraction and hydrolysis to liberate beta-cryptoxanthin (free). The extracts prepared from pulp and skin showed 1 mg/100 g and 8 mg/100 g beta-cryptoxanthin, respectively, and useful applications in functional foods (H. Takahashi and Y. Inada, U.S. Pat. Appl. Pub. No. 2007/0116818 A, published 24 May 2007, Extract containing beta-cryptoxanthin from Persimmon fruit). Shirakura et. al (2008) and Takayanagi and Mukai (2008) have developed commercial processes for enzyme treated Satsuma mandarin (EPSM) and emulsified mandarin extract (EME) containing 0.2 and 0.05% beta-cryptoxanthin, respectively. They reported that the extracts possess reduction of visceral fat and plasma glucose in a human comparative trial designed as placebo-controlled double blind study (Y. S. Hirakura, K. Takayanagi and K. Mukai, Reducing effect of beta-cryptoxanthin extracted from Satsuma mandarin on human body fat, Abstract, page 161; K. Takayanang and K. Mukai, Abstract: Beta-cryptoxanthin and Satsuma mandarin: Industrial production and health promoting benefits, page, 73, Carotenoid Science, 12 Jun. 2008, Abstracts of the papers presented at the 15$^{th}$ International Symposium on Carotenoids, Okinawa, Japan, 22$^{nd}$-27$^{th}$ Jun., 2008).

Biotechnological Production

Serrato-Joya et al. (2006) have generated beta-cryptoxanthin in a laboratory scale batch production using *Flavobacterium lutescens* ITC B 008 (O. Serrato-Joya, H. Jimenez-Islas, E. Botello-Alvarez, R. Nicomartinez, and J. L. Navarrete-Bolans, Process of beta-cryptoxanthin, a provitamin A precursor by *Flavobacterium Lutescens*, J. Food Sci. 71, E314-E319, 2006). Louie and Fuerst (2008) disclosed a method for preparing beta-cryptoxanthin from a microorganism transformed with the beta-carotene hydroxylase gene from *Arabidopsis thaliana* by culturing the transformant and recovering beta-cryptoxanthin (U.S. Pat. Appl. Pub. No. 2008/0124755, published 29 May 2008, Biosynthesis of beta-cryptoxanthin in microbial hosts using *Arabidopsis thaliana* beta-carotene hydroxylase gene). Again, Louie and Fuerst (2009) disclosed a method of beta-cryptoxanthin production by the use of lycopene beta-monocyclase and converting lycopene to beta-cryptoxanthin through gamma-carotene and 3-hydroxy-gamma-carotene (M. Y. Louie and E. J. Fuerst, U. S. Pat. Appl. Pub. No. 2009/093015, published 9 Apr. 2009, Beta-cryptoxanthin production using a novel lycopene beta-monocyclase gene). Hoshino et al. (2006) have disclosed a process for producing zeaxanthin and beta-cryptoxanthin which comprises cultivating a recombinant microorganism expressing beta-carotene hydroxylase gene (Phaffia) under aerobic conditions in aqueous nutrient media and isolating the resulting carotenoids from the cells of the recombinant microorganism or from the broth (T. Hoshino, K. Ojima and Y. Setoguchi, U.S. Pat. Appl. Pub. No. 2006/0121557, published 8 Jun. 2006, Process for producing zeaxanthin and beta-cryptoxanthin).

No microorganism appears able to naturally produce beta-cryptoxanthin as the final product, and hence fermentation technology is not feasible for commercial production. Further, in the fermentation processes the carotenoids produced are low in concentration and as complex mixtures of products, including various added ingredients. Extensive purification steps require large amounts of solvents and the generation of considerable amounts of by-products.

Synthetic Production

Khachik and coworkers developed three processes for the preparation of beta-cryptoxanthin. Two methods employ lutein or lutein esters as the starting material and in the presence of acid it is converted into three forms of anhydroluteins: 3-hydroxy-3',4'-didehydro-beta-gamma-carotene (I), 3-hydroxy-2',3'-didehydro-beta-epsilon-carotene (II) and 3-hydroxy-3',-4'-didehydro-beta-beta-carotene (III). The mixture of anhydroluteins rich in anhydrolutein (III) was subjected to ionic hydrogenation in the presence of an acid and chlorinated solvent to produce alpha- and beta-cryptoxanthin. The purified product showed total carotenoids 85%, of which beta-cryptoxanthin was 55 to 61%, alpha-cryptoxanthin 18 to 30%, and the remainder 3 to 8% R,R-zeaxanthin and un-reacted anhydroluteins (F. Khachik, U.S. Pat. No. 7,115,786 B2, Oct. 3, 2006, Method for production of beta-cryptoxanthin and alpha-cryptoxanthin from commercially available lutein; F. Khachik, A. N. Chang, A. Gana and E. Mazzola, Partial synthesis of (3R, 6'R)-alpha-cryptoxanthin and (3R)-beta-cryptoxanthin from (3R,3'R,6'R)-lutein (J. Nat. Products 70, 220-226, 2007)).

In the second method, the mixture of anhydroluteins were converted to alpha- and beta-cryptoxanthin by catalytic hydrogenation using platinum supported on alumina. The final product was reddish crystals with total carotenoids 60% and the HPLC composition showing beta-cryptoxanthin and alpha-cryptoxanthin in the ratio 3:1, 7:3, or 5:1 and the presence of un-reacted anhydroluteins I and II and R,R-zeaxanthin.

In the third method, the process is for the synthesis of optically active 3-hydroxy-beta-ionone and transformation to beta-cryptoxanthin using Wittig coupling reactions. The synthetic approach involves multiple step reactions and purifications leading to a mixture of beta-cryptoxanthin and R,R-zeaxanthin (F. Khachik and A. N. Chang, U.S. Pat. Appl. Pub. No. 2009/0311761, published 17 Dec. 2009, Process for synthesis of 3(S)- and (3R)-3-hydroxy-beta-ionone and their transformation to zeaxanthin and beta-cryptoxanthin; Synthesis of (3S)- and (3R)-hydroxy-beta-ionone and their transformation into (3S)- and (3R)-beta-cryptoxanthin, Synthesis 3, 509-516, 2011).

The Present Invention

As demonstrated by the discussion above, prior processes for producing beta-cryptoxanthin have several limitations. While natural sources of beta-cryptoxanthin are available, extracts have thus far been produced only in enriched form in fruit drinks such as tangerine, Satsuma orange and persimmon. The use of a biotechnological route for producing beta-cryptoxanthin is still in preliminary development and has thus far been limited to laboratory scale production with poor yields. The synthetic approach gives a mixture of beta-cryptoxanthin and a considerable amount of impurities such as alpha-cryptoxanthin, which is most likely zeinoxanthin (a non-provitamin A), along with un-reacted anhydroluteins and zeaxanthin. Applying the processes of Khachik and coworkers, the separation of beta-cryptoxanthin is complex, involves multiple steps and is not commercially feasible. Thus, a need exists for natural beta-cryptoxanthin concentrates of high purity and a process for producing the same.

Based on the chemical structure of anhydrolutein II (3-Hydroxy-2',3'-didehydro-beta,epsilon-carotene), one would expect hydrogenation at 2',3'-double bond to form zeinoxanthin (beta,epsilon-caroten-3-ol). In addition, one would expect no conversion of zeinoxanthin to beta-cryptoxanthin by alkali isomerization due to the absence of allylic hydroxyl group. This has been confirmed by phenyl carbinol alkali catalyzed reaction at high temperature (110° C.) of beta-cryptoxanthin containing zeinoxanthin 10% (by HPLC), where after the resultant product showed no change in HPLC profile compared to the control. In fact, the base catalyzed reaction of so called alpha-cryptoxanthin failed to arrive at beta-cryptoxanthin (F. Khachik, A. N. Chang, A. Gana and E. Mazzola, Partial synthesis of 3(R,6'R)-alpha-cryptoxanthin and (3R)-beta-cryptoxanthin from (3R,3R', 6'R)-lutein, J. Nat. Prod. 70, 220-226, 2007).

Review of the art demonstrates the general unavailability of high purity beta-cryptoxanthin, produced in appreciable amounts, as a major ingredient derived from natural sources for use as a nutritional ingredient and in dietary supplements. A primary reason for the unavailability of beta-cryptoxanthin from natural sources (particularly fruits and vegetables) is its low concentration in natural sources, preventing commercialization of this molecule by traditional solvent based extraction procedures. Identifying a source and process to provide commercially available beta-cryptoxanthin concentrates of high purity would help to meet the need for this product and help establish the potential health benefits of beta-cryptoxanthin in clinical trials and as dietary supplements. *Capsicum* extract has a reasonably high content of beta-cryptoxanthin, but there are many other promising options of beta-cryptoxanthin-containing materials. The present invention meets the need in the art and provides natural beta-cryptoxanthin concentrates of high purity from plant oleoresin, particularly *Capsicum* oleoresin, and a process for its preparation. In addition, these natural beta-cryptoxanthin concentrates can be used to provide several health benefits, for example in bone loss and osteoporosis.

Bone mass decreases with increasing age. This decrease is due to increased bone resorption and reduced bone formation. The decrease in bone mass induces osteoporosis (M. Yamaguchi, S. Uchiyama, K. Ishiyama, and K. Hashimoto, Oral Administration in Combination with Zinc Enhances Beta-cryptoxanthin-Induced Anabolic Effects on Bone Components in the Femoral Tissues of Rats In Vivo, Biol. Pharm. Bull. 29(2) 371-374 (2006)). Bone homeostasis is maintained through a balance between osteoblastic bone formation and osteoclastic bone resorption (M. Yamaguchi, Role of Carotenoid Beta-Cryptoxanthin in Bone Homeostasis, Journal of Biomedical Science 19-36 (2012)). Production of estrogen decreases in menopause causing an imbalance in metabolism (*Citrus unshiu* extract. Health Ingredient for prevention of osteoporosis health ingredient for whitening and aesthetic ingredient for cosmetic, Product monograph, Ver.3.0HS by *Oryza* Oil & Fat Chemical Co Ltd.). Beta-cryptoxanthin has been found to have a potential anabolic effect on bone due to stimulating osteoblastic bone formation and inhibiting osteoclastic bone resorption. Oral administration of beta-cryptoxanthin may have a preventive effect on bone loss with increasing age and on osteoporosis. For example, the role of beta-cryptoxanthin obtained from a *Capsicum* source in strengthening bone and inhibiting bone resorption is demonstrated in Example 4 below with ovariectomized female wistar rats.

BRIEF SUMMARY OF THE INVENTION

An objective of the present invention is to provide natural beta-cryptoxanthin concentrates of high purity, which are safe for human consumption and useful for nutrition and health care, including bone health, and a process for their preparation from a natural source material.

In some embodiments the present invention provides a process for the isolation of beta-cryptoxanthin crystals containing at least about 80% by weight of total xanthophylls (total carotenoids) in free form, out of which the trans-beta-cryptoxanthin content is at least about 98.5% by weight, the remaining including trace amounts of zeaxanthin, trans-capsanthin, beta-carotene and other carotenoids derived from oleoresin and extracts of plant materials such as *Capsicum* sources.

In some embodiments the present invention provides a process for the preparation of beta-cryptoxanthin crystals containing at least about 40% by weight of total carotenoids, out which the trans-beta-cryptoxanthin is at least about 90% by weight, the remaining including trace amounts of zeaxanthin, trans-capsanthin, beta-carotene and other carotenoids derived from oleoresin and extracts of plant materials such as *Capsicum* sources.

In some embodiments the present invention provides a process for the preparation of beta-cryptoxanthin crystals containing at least about 10% by weight of total carotenoids, out of which the trans-beta-cryptoxanthin is at least about 75% by weight, the remaining including zeaxanthin, trans-capsanthin, beta-carotene and traces amounts of other carotenoids derived from oleoresin and extracts of plant materials such as *Capsicum* sources.

In some embodiments the present invention provides a process for the preparation of beta-cryptoxanthin crystals containing total carotenoids about 10 to 80% by weight, out of which the trans-beta-cryptoxanthin content is in the range of about 75 to 98% by weight, the rest including zeaxanthin, trans-capsanthin, beta-carotene and trace amounts of other carotenoids derived from a starting material like saponified *Capsicum* extract.

In certain aspects the present invention provides a simple and convenient process for the preparation of high purity beta-cryptoxanthin from *capsicum* oleoresin or saponified *capsicum* extract. In some aspects the present invention provides residual solvent-free beta-cryptoxanthin crystals, in which trans-beta-cryptoxanthin forms the major ingredient in the total carotenoids. A feature of the present invention provides recovery of carotene hydrocarbon fractions rich in beta-carotene from the process described herein. In other aspects, the present invention provides recovery of a xanthophylls fraction comprising mainly zeaxanthin and trans-capsanthin having high antioxidant properties.

In some embodiments the process for obtaining the high purity trans-beta-cryptoxanthin described in the present invention is achieved by:

saponification of esterified xanthophylls in *Capsicum* extract, which results in free xanthophylls and which is purified by washing with acidified water, followed by drying to obtain a carotenoid mass;

treating the carotenoid mass with non-polar solvent under stirring, followed by filtration and concentration to obtain a mass;

subjecting the mass to column chromatography using silica gel and elution using non-polar solvent to remove beta-carotene;

eluting the column with non-polar solvent containing about 2% polar solvent, and obtaining an eluent after concentration of a concentrate showing about 10% total carotenoids by weight, of which trans-beta-cryptoxanthin comprises about 75% by weight;

treating the above concentrate with ethanol under stirring, followed by cooling to about 10° C. and filtering to obtain a semi-purified crystalline mass showing total xanthophylls about 40% by weight, of which trans-beta-cryptoxanthin comprises about 98% by weight; and washing the crystalline mass with hexane containing about 20% ethyl acetate, cooling to about −10° C. and filtering to obtain a high purity crystalline material showing about 80% total xanthophylls by weight, of which trans-beta-cryptoxanthin comprises about 98.5% by weight.

In some aspects, the present invention provides a process for the preparation of a beta-cryptoxanthin enriched concentrate from plant material comprising about 10-80% by weight total xanthophylls, of which about 75-98% by weight is trans-beta-cryptoxanthin, the process comprising: (a) mixing an oleoresin of plant material comprising xanthophylls esters with an aliphatic alcoholic solvent; (b) saponifying the xanthophylls esters present in the oleoresin with an alkali at an elevated temperature; (c) removing the aliphatic alcoholic solvent followed by addition of water to obtain a diluted resultant mixture; (d) adding a diluted organic acid to the diluted resultant mixture to form a water layer and a precipitated xanthophylls mass; (e) removing the water layer and washing the precipitated xanthophylls mass with a polar solvent; (f) drying the precipitated xanthophylls mass to obtain a crude xanthophylls mass; (g) washing the crude xanthophylls mass with a non-polar solvent and concentrating the non-polar solvent washings to obtain a concentrated crude xanthophylls mass; (h) transferring the concentrated crude xanthophylls mass to a silica gel column and washing with a non-polar solvent; (i) eluting the column with a mixture of non-polar and polar solvent and concentrating the elutions to obtain a trans-beta-cryptoxanthin-rich xanthophylls concentrate; (j) admixing the trans-beta-cryptoxanthin-rich xanthophylls concentrate with an aliphatic alcohol and then cooling; and (k) filtering and drying the trans-beta-cryptoxanthin-rich xanthophylls concentrate to obtain a purified trans-beta-cryptoxanthin concentrate.

In some embodiments, the xanthophylls esters in the oleoresin of plant material in step (a) are present at about 6-8% by weight. In some embodiments, the aliphatic alcohol of step (a) or (j) is selected from the group consisting of ethanol, methanol, isopropyl alcohol, and mixtures thereof. In some embodiments, the ratio of oleoresin to alcohol in step (a) ranges from about 1:0.25 to about 1:1 weight/volume. In some embodiments, the alkali of step (b) is selected from the group consisting of sodium hydroxide, potassium hydroxide, and mixtures thereof. In some embodiments, the ratio of oleoresin to alkali in step (b) ranges from about 1:0.25 to 1:0.5 weight/weight. In some embodiments, the elevated temperature of step (b) ranges from about 75 to about 85° C. In some embodiments, the addition of water in step (c) is about 5 times that of the oleoresin (weight/weight). In some embodiments, the diluted organic acid of step (d) is acetic acid or phosphoric acid. In some embodiments, the diluted organic acid of step (d) is a solution of about 20% to about 50% organic acid. In some embodiments, the polar solvent of step (e) is water. In some embodiments, the non-polar solvent of steps (g), (h), and (i) is selected from the group consisting of a hexane, a pentane, a heptane, and mixtures thereof. In some embodiments, the crude xanthophylls mass and non-polar solvent of step (g) are in a ratio of about 1:10 to 1:15 weight/volume.

In some embodiments, the concentrated crude xanthophylls mass of step (g) comprises beta-carotene, trans-beta-cryptoxanthin, trans-capsanthin, zeaxanthin, and trace amounts of other carotenoids, such as capsorubin or violaxanthin.

In some embodiments, the concentrated crude xanthophylls mass and the non-polar solvent of step (h) are in a ratio of about 1:5 to 1:8 weight/volume. In some embodiments, a carotene concentrate is obtained by distilling the non-polar solvent washing of step (h). In further embodiments, wherein the carotene concentrate is beta-carotene.

In some embodiments, the polar solvent of step (i) is selected from the group consisting of a propanone, a pentanone, and mixtures thereof. In some embodiments, the non-polar solvent and polar solvent of step (i) are in a ratio of about 95:5 to about 98:2. In some embodiments, the trans-beta-cryptoxanthin-rich xanthophylls concentrate of step (i) comprises at least about 10% by weight of total xanthophylls, of which trans-beta-cryptoxanthin content is at least about 75% by weight. In some embodiments, the cooling in step (j) is performed at about 10° C. In some embodiments, the purified trans-beta-cryptoxanthin concentrate of step (k) comprises at least about 40% by weight of total xanthophylls, of which trans-beta-cryptoxanthin content is at least about 90% by weight.

In some embodiments, the process further comprises a step (l): washing the purified trans-beta-cryptoxanthin concentrate with a mixture of non-polar and ester solvent and cooling for precipitation to obtain high purity trans-beta-cryptoxanthin crystals. In some embodiments, the high purity trans-beta-cryptoxanthin crystals of step (l) comprises at least about 80% by weight of total xanthophylls, of which trans-beta-cryptoxanthin content is at least about 98% by weight. In some embodiments, the ester solvent of step (l) is ethyl acetate and the non-polar solvent of step (l) is hexane. In some embodiments, the non-polar solvent and ester solvent of step (l) are in a ratio of about 80:20 to about 90:10. In some embodiments, the temperature for cooling in step (l) is about −10° C.

In some embodiments, the invention provides a process for the preparation of a beta-cryptoxanthin enriched concentrate from plant material comprising at least about 80% by weight total xanthophylls, of which at least about 98% by weight is trans-beta-cryptoxanthin, the process comprising: (a) mixing an oleoresin of plant material comprising xanthophylls esters with ethanol, wherein the ratio of oleoresin to ethanol is about 1:1 weight/volume; (b) saponifying the xanthophylls esters present in the oleoresin with potassium hydroxide without addition of water, wherein the ratio of oleoresin to potassium hydroxide is about 1:0.25 weight/weight; (c) applying heat to the oleoresin to elevate the temperature up to reflux at about 80-85° C.; (d) agitating the oleoresin for about 3 to 5 hours at about 80-85° C.; (e) evaporating the ethanol under vacuum followed by addition of water at about 5 times that of the oleoresin (weight/weight) to obtain a diluted resultant mixture and agitating for about 1 hour; (f) neutralizing the diluted resultant mixture with about 25% acetic acid to form a water layer and a precipitated xanthophylls mass; (g) separating the water layer from the precipitated xanthophylls mass and washing the mass with water to remove soaps and other polar soluble materials; (h) drying the precipitated xanthophylls mass under vacuum to obtain a crude xanthophylls mass; (i) washing the crude xanthophylls mass with about 1:10 hexane (weight/volume) and concentrating the hexane washings to obtain a concentrated crude xanthophylls mass; (j) transferring the concentrated crude xanthophylls mass to a silica gel column at a ratio of about 1:5 (weight/weight) and eluting with hexane to obtain a carotene fraction; (k) washing the column with about 98:2 hexane to acetone and concentrating the washings to obtain a trans-beta-cryptoxanthin-rich xanthophylls concentrate; (l) admixing the trans-beta-cryptoxanthin-rich xanthophylls concentrate with about 1:2 ethanol under stirring and then cooling at about 10° C. for about 8 hours; (m) filtering and drying the trans-beta-cryptoxanthin-rich xanthophylls concentrate under vacuum to obtain a purified trans-beta-cryptoxanthin concentrate; and (n) washing the purified trans-beta-cryptoxanthin concentrate with about 80:20 hexane:ethylacetate and cooling to about −10° C. for about 18 hours for precipitation to obtain high purity trans-beta-cryptoxanthin crystals.

In some embodiments, the total xanthophylls of the processes comprise by-products selected from zeaxanthin, trans-capsanthin, beta-carotene, trace amounts of other carotenoids, and any combinations thereof.

In aspects of the invention, the plant material used in the processes or to derive the beta-cryptoxanthin concentrates is selected from the group consisting of fruits, vegetables, and mixtures thereof. In some embodiments, the plant material is from a *capsicum*.

In aspects of the invention, a beta-cryptoxanthin concentrate is obtained by the processes of the invention.

In certain aspects of the invention, the beta-cryptoxanthin concentrate is in a dosage form selected from beadlets, microencapsulated powders, oil suspensions, liquid dispersions, capsules, pellets, ointments, soft gel capsules, tablets, chewable tablets or lotions/liquid preparations. In aspects, the beta-cryptoxanthin concentrate is added to a composition.

In certain aspects, the present invention provides a composition comprising beta-cryptoxanthin concentrate derived from plant material, wherein said concentrate comprises at least about 10% by weight total xanthophylls, of which at least about 75% by weight is trans-beta-cryptoxanthin. In some embodiments, the total xanthophylls comprise by-products selected from zeaxanthin, trans-capsanthin, beta-carotene, trace amounts of other carotenoids such as capsorubin or violaxanthin, and combinations thereof. In some embodiments, the composition further comprises a pharmaceutically acceptable ingredient or a food grade ingredient.

In some embodiments, the total xanthophylls of the beta-cryptoxanthin concentrate comprise by-products selected from the group consisting of zeaxanthin, trans-capsanthin, beta-carotene, trace amounts of other carotenoids such as capsorubin or violaxanthin, and combinations thereof.

In aspects of the invention, the beta-cryptoxanthin concentrate is used in a dietary supplement for protection against the development of rheumatoid, inflammatory arthritis.

In certain aspects, the present invention provides methods for treating individuals suffering from a condition that can be treated with the beta-cryptoxanthin concentrates of the inventions. In some embodiments, the present invention provides a method for the prophylaxis of the development of rheumatoid, inflammatory arthritis, or bone diseases, comprising administering to a patient in need thereof a therapeutically effective amount of a beta-cryptoxanthin concentrate derived from plant material, wherein said concentrate comprises at least about 10% by weight total xanthophylls, of which at least about 75% by weight is trans-beta-cryptoxanthin. In some embodiments, the present invention provides a method for strengthening of bone, comprising administering to a patient in need thereof a therapeutically effective amount of a beta-cryptoxanthin concentrate derived from plant material, wherein said concentrate comprises at least about 10% by weight total xanthophylls, of which at least about 75% by weight is trans-beta-cryptoxanthin. In some embodiments, the present invention provides a method for inhibiting bone resorption, comprising administering to a patient in need thereof a therapeutically effective amount of a beta-cryptoxanthin concentrate derived from plant material, wherein said concentrate comprises at least about 10% by weight total xanthophylls, of which at least about 75% by weight is trans-beta-cryptoxanthin. In some embodiments, the beta-cryptoxanthin concentrate is administered in an amount from about 0.0001 mg/kg to about 10 m/kg.

BRIEF DESCRIPTION OF THE DRAWINGS/FIGURES

DETAILED DESCRIPTION OF THE INVENTION

Figure 1:
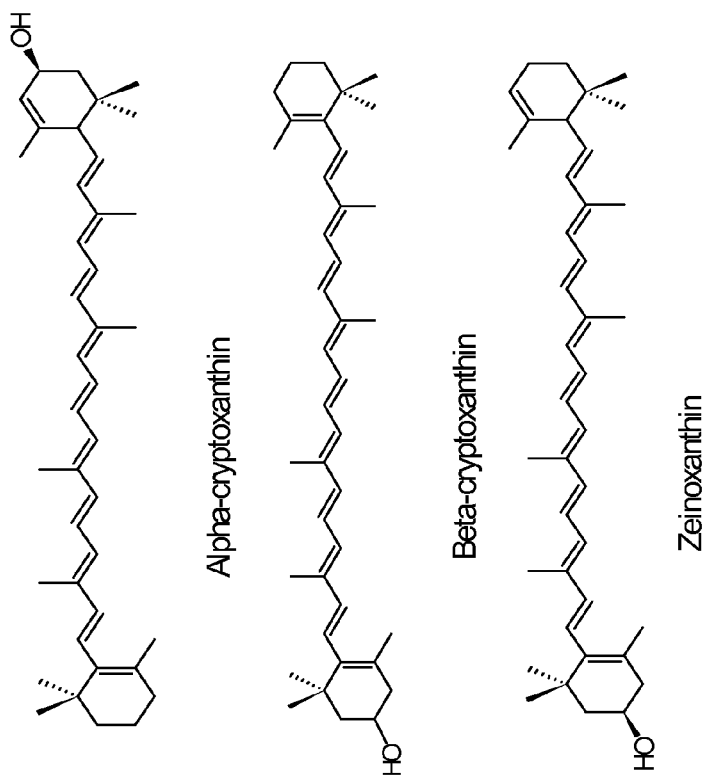
FIG. 1 depicts the chemical structures of alpha-cryptoxanthin, beta-cryptoxanthin and zeinoxanthin.

The product and the process of the present invention is described herein below which is illustrative as shown in the examples and should not be construed to limit the scope of the present invention in any manner whatsoever.

Definitions

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus.

Also, the indefinite articles "a" and "an" preceding an element or component of the invention are intended to be nonrestrictive regarding the number of instances, that is, occurrences of the element or component. Therefore, "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. For example, depending on the level of precision of the instrumentation used, standard error based on the number of samples measured, and rounding error, the term "about" includes, without limitation, ±10%.

Units, prefixes, and symbols are denoted in their Systéme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

Beta-Cryptoxanthin Concentrate

The present invention provides a beta-cryptoxanthin concentrate, which contains about 10-80% by weight total xanthophylls, of which about 75-98% by weight is trans-beta-cryptoxanthin, the remaining including zeaxanthin, trans-capsanthin, beta-carotene and trace amounts of other carotenoids, derived from oleoresin or extract of plant material and which is useful for nutrition and health care.

In certain embodiments, the concentrate comprises at least about 10% by weight total xanthophylls, of which at least about 75% by weight is trans-beta-cryptoxanthin.

In certain embodiments, the concentrate comprises at least about 40% by weight total xanthophylls, of which at least about 90% by weight is trans-beta-cryptoxanthin.

In certain embodiments, the concentrate comprises at least about 80% by weight total xanthophylls, of which at least about 98% by weight is trans-beta-cryptoxanthin.

Natural Sources

The plant material is derived from sources including, but not limited to, fruits and vegetables. In some embodiments of the invention, the plant material is derived from capsicums. *Capsicum* is a genus of flowering plants that includes several varieties of peppers, such as but not limited to red peppers, and the word "*capsicum*" is also used interchangeably in several parts of the world when referring to peppers. The *capsicum* oleoresin described herein also includes paprika oleoresin.

Dosage and Administration

The beta-cryptoxanthin enriched concentrates of the invention can be formulated in a dosage form including, but not limited to, beadlets, microencapsulated powders, oil suspensions, liquid dispersions, capsules, pellets, ointments, soft gel capsules, tablets, chewable tablets or lotions/liquid preparations. The beta-cryptoxanthin enriched concentrates of the invention can also be provided in a food or feed (including liquid or solid) composition. Thus, it is envisioned that suitable delivery methods include, but are not limited to, oral, parenteral, subcutaneous, intravenous, intramuscular, intraperitoneal, transdermal, intracranial, or buccal administration.

Compositions comprising the trans-beta-cryptoxanthin enriched concentrates of the invention include one or more suitable pharmaceutically acceptable ingredients or food grade ingredients such as, but not limited to, carriers, binders, stabilizers, excipients, diluents, pH buffers, disintegrators, solubilizers and isotonic agents.

The compositions of the invention may include a "therapeutically effective amount" or a "prophylactically effective amount" of the trans-beta-cryptoxanthin enriched concentrates. A "therapeutically effective amount" refers to an amount effective, at dosages and for periods of time necessary, to achieve the desired therapeutic result, for example in methods of treatment or pharmaceutical compositions for use in such methods. A therapeutically effective amount may vary according to factors such as the disease state, age, sex, and weight of the individual. A therapeutically effective amount is also one in which any toxic or detrimental effects of the composition are outweighed by the therapeutically beneficial effects. A "prophylactically effective amount" refers to an amount effective, at dosages and for periods of time necessary, to achieve the desired prophylactic or preventive result. Typically, since a prophylactic dose is used in subjects prior to or at an earlier stage of disease or a condition requiring treatment is identified, the prophylactically effective amount will be less than the therapeutically effective amount.

Dosage amounts useful for administering the trans-beta-cryptoxanthin enriched concentrates of the invention can range, e.g., from about 0.0001 mg/kg to about 10 mg/kg, from about 0.001 mg/kg to about 1.0 mg/kg, and more usually from about 0.01 mg/kg to about 0.5 mg/kg, from about 0.01 mg/kg to about 0.1 mg/kg, from about 0.01 mg/kg to about 0.05 mg/kg, from about 0.01 mg/kg to about 0.025 mg/kg, from about 0.01 mg/kg to about 0.2 mg/kg, or from about 0.05 mg/kg to about 5 mg/kg, from about 0.05 mg/kg to about 1.0 mg/kg, or from about 0.05 mg/kg to about 0.1 mg/kg of the host body weight. For example dosages can be about 0.005 mg/kg body weight, about 0.01 mg/kg body weight, about 0.05 mg/kg body weight, about 0.1 mg/kg body weight, about 1.0 mg/kg body weight, or about 10 mg/kg body weight or within the range of about 0.001-1.0 mg/kg, preferably at least 0.005 mg/kg. Doses intermediate in the above ranges are also intended to be within the scope of the invention (e.g., about 0.002 mg/kg, about 0.025 mg/kg, about 0.05 mg/kg, about 0.075 mg/kg, about 0.1 mg/kg, about 0.2 mg/kg, about 2 mg/kg, etc.). Subjects can take doses daily or be administered such doses daily, on alternative days, weekly or according to any other schedule determined by empirical analysis. An exemplary treatment entails administration in multiple dosages over a prolonged period, for example, of at least six months.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms of the invention are dictated by and directly dependent on (a) the unique characteristics of the trans-beta-cryptoxanthin enriched concentrates of the invention and the particular therapeutic or prophylactic effect to be achieved, and (b) the limitations inherent in the art of compounding such trans-beta-cryptoxanthin enriched concentrates of the invention for treatment sensitivity in mammalian subjects. The individuals or mammalian subjects of the invention can include both human and animal subjects including domestic animals, pets, and farm-raised fish.

Processes

The present invention provides a process for the preparation of beta-cryptoxanthin enriched concentrate from plant material comprising about 10-80% by weight total xanthophylls, of which about 75-98% by weight is trans-beta-cryptoxanthin, the remaining including zeaxanthin, trans-capsanthin, beta-carotene and trace amounts of other carotenoids, suitable for human consumption as nutritional supplements, the process comprising:
  a) Mixing xanthophylls esters in an oleoresin with an aliphatic alcohol solvent;
  b) Saponifying the xanthophylls esters present in the oleoresin of plant material with an alkali at an elevated temperature;
  c) Removing the aliphatic alcoholic solvent followed by addition of water to get diluted resultant mixture;
  d) Adding a diluted organic acid to the diluted resultant mixture to form a water layer and a precipitated xanthophylls mass;
  e) Removing the water layer and washing the precipitated xanthophylls mass with a polar solvent;
  f) Drying the precipitated xanthophylls mass to obtain a crude xanthophylls mass;
  g) Washing the crude xanthophylls mass with a non-polar solvent and concentrating the non-polar solvent washings to get a concentrated crude xanthophylls mass;
  h) Transferring the concentrated crude xanthophylls mass to a silica gel column and washing with a non-polar solvent;
  i) Eluting the column with a mixture of non-polar and polar solvent and concentrating the elutions to obtain a trans-beta-cryptoxanthin-rich xanthophylls concentrate;
  j) Admixing the trans-beta-cryptoxanthin-rich concentrate with an aliphatic alcohol and then cooling; and
  k) Filtering and drying the trans-beta-cryptoxanthin-rich xanthophylls concentrate to obtain a purified trans-beta-cryptoxanthin concentrate.

In certain embodiments, the xanthophylls esters in the oleoresin of plant material are present at about 2-12% by weight, about 4-10% by weight, or about 6-8% by weight.

In certain embodiments, the aliphatic alcohol comprises a hydrocarbon fragment derived from a fatty, nonaromatic hydrocarbon and is selected from the group consisting of ethanol, methanol, isopropyl alcohol, and mixtures thereof. In some embodiments, the aliphatic alcohol is ethanol.

In certain embodiments, the ratio of oleoresin to alcohol ranges from about 1:0.25 to about 1:1 weight/volume. In some embodiments, the ratio is about 1:1, about 1:0.75, or about 1:50.

In certain embodiments, the alkali is a soluble hydroxide of the alkali metals, including lithium, sodium, potassium, rubidium, or cesium, and is selected from the group consisting of sodium hydroxide, potassium hydroxide, and mixtures thereof. In some embodiments, the alkali is sodium hydroxide. In other embodiments, the alkali is potassium hydroxide.

In certain embodiments, the ratio of oleoresin to alkali ranges from about 1:0.25 to about 1:0.5 weight/weight. In some embodiments, the ratio is about 1:0.25.

In certain embodiments, the elevated temperature for saponification is above room temperature. In some embodiments, the elevated temperature ranges from about 65 to about 95° C., about 70 to about 90° C. about 75 to about 85° C., from about 75 to about 80° C., or from about 80 to about 85° C.

In certain embodiments, the water added to form the diluted resultant mixture in step (c) above is about 2 to about 10 times, about 3 to about 9 times, about 4 to about 8 times, or about 5 to about 7 times that of the oleoresin (weight/weight). In some embodiments the water added is about 4 times, about 5 times, or about 6 times that of the oleoresin (weight/weight). In some embodiments, the water added is about 5 times that of the oleoresin (weight/weight).

In certain embodiments, the diluted organic acid used in the process is acetic acid or phosphoric acid. In certain embodiments, the diluted organic acid is a solution of about 20% to about 50% of organic acid. In some embodiments, the diluted organic acid is about 20% to about 30%, about 30% to about 40%, about 40% to about 50%, about 20% to about 40%, about 30% to about 50% of organic acid. In some embodiments, the diluted organic acid is about 20%, about 25%, about 30%, about 35%, about 40%, about 45%, or about 50% of organic acid.

In certain embodiments, the polar solvent used to wash the precipitated xanthophylls mass is water.

In certain embodiments, the non-polar solvent used in the process is selected from the group consisting of a hexane, a pentane, a heptane, and mixtures thereof.

In certain embodiments, the crude xanthophylls mass and the non-polar solvent are in a ratio of about 1:5 to about 1:20 weight/volume, about 7.5 to about 17.5 weight/volume, or about 1:10 to about 1:15 weight/volume.

In certain embodiments, the concentrated crude xanthophylls mass and the non-polar solvent are in a ratio of about 1:2 to about 1:14 weight/volume, about 1:3 to about 1:12 weight/volume, about 1:4 to about 1:10 weight/volume, or about 1:5 to about 1:8 weight/volume.

In certain embodiments, a carotene concentrate is obtained by distilling the non-polar solvent washing in step (h) above. In certain embodiments, the carotene concentrate is beta-carotene.

In certain embodiments, the polar solvent used in the process is selected from the group consisting of a propanone, a pentanone, and mixtures thereof.

In certain embodiments, the non-polar solvent and polar solvent in step (i) above are in a ratio of about 90:10 to about 99:1, about 92.5 to about 99:1, about 94:6 to about 98:2, or about 95:5 to about 98:2 (volume/volume).

In certain embodiments, the temperature used to cool the trans-beta-cryptoxanthin-rich xanthophylls concentrate is from about 5° C. to about 15° C. or about 7.5° C. to about 12.5° C. In some embodiments, the temperature is about 7° C., about 8° C., about 9° C., about 10° C., about 11° C., or about 12° C.

In certain embodiments, the trans-beta-cryptoxanthin-rich xanthophylls concentrate comprises at least about 10% by weight of total xanthophylls, of which trans-beta-cryptoxanthin content is at least about 75% by weight.

In certain embodiments, the purified trans-beta-cryptoxanthin concentrate comprises at least about 40% by weight of total xanthophylls, of which trans-beta-cryptoxanthin content is at least about 90% by weight.

In certain embodiments, the process above further comprises a step (l): washing the purified trans-beta-cryptoxanthin concentrate with a mixture of non-polar and ester solvent and cooling for precipitation to obtain high purity trans-beta-cryptoxanthin crystals.

In certain embodiments, the high purity trans-beta-cryptoxanthin crystals of step (l) comprises at least about 80% by weight of total xanthophylls, of which trans-beta-cryptoxanthin content is at least about 98% by weight.

In certain embodiments, the ester solvent of step (l) is ethyl acetate and the non-polar solvent of step (l) is hexane.

In certain embodiments, the non-polar solvent and ester solvent of step (l) are in a ratio of about 70:30 to about 90:10, about 80:20 to about 90:10, about 75:25 to about 95:5, or about 85:15 to about 95:5 (volume/volume).

In certain embodiments, the temperature for cooling in step (l) above is from about −5° C. to about −15° C. or about −7.5° C. to about −12.5° C. In some embodiments, the temperature for cooling in step (l) above is about −7° C., about −8° C., about −9° C., about −10° C., about −11° C., about −12° C.

In certain embodiments, the total xanthophylls comprise by-products selected from zeaxanthin, trans-capsanthin, beta-carotene, trace amounts of other carotenoids, and any combinations thereof. In some embodiments, the trace amounts of other carotenoids include capsorubin or violaxanthin.

In certain embodiments, the plant material is selected from the group consisting of fruits, vegetables, and mixtures thereof. In some embodiments, the plant material is from a *capsicum*.

In certain embodiments, the solvent used in the process is removed by methods including, but not limited to, evaporation under vacuum. In certain embodiments, the saponification of the xanthophylls esters is carried out for at least 2 hours with agitation. In some embodiments, the saponification is carried out for about 2 to about 20 hours, about 2 to about 15 hours, about 2 to about 10 hours, about 3 to about 8 hours, about 3 to about 6 hours, or about 3 to about 5 hours.

In some embodiments, the non-polar hydrocarbon solvent used in the process is hexane or mixture of low boiling hydrocarbons, such as pentane or heptane. In some embodiments, the aliphatic alcohol selected for saponification is ethanol and the alkali used is selected from sodium or potassium hydroxide.

In some embodiments, the silica gel column containing xanthophylls concentrate is eluted with non-polar solvent to remove the carotenes to obtain beta-cryptoxanthin concentrate.

In some embodiments, the process comprises further washing the columns with non-polar:polar solvent and concentrating the washing results in beta-cryptoxanthin concentrate comprising about 10% by weight total xanthophylls out of which trans-beta-cryptoxanthin content is at least about 75% by weight and the remaining being beta-carotene, trans-capsanthin, zeaxanthin and traces of other carotenoids. The purified beta-cryptoxanthin concentrate comprises at least about 40% by weight of total xanthophylls out of which trans-beta-cryptoxanthin content is at least about 90% by weight and the high purity beta-cryptoxanthin concentrate obtained by washing the purified beta-cryptoxanthin concentrate with a mixture of non-polar:ester solvent and cooling for precipitation results in a concentrate which comprises at least about 80% by weight of total xanthophylls out of which trans-beta-cryptoxanthin content is at least about 98% by weight, the rest being beta-carotene, zeaxanthin, trans-capsanthin and traces of other carotenoids.

In one embodiment, the present invention provides for the preparation of a beta-cryptoxanthin enriched concentrate from plant material comprising at least about 80% by weight total xanthophylls, of which at least about 98% by weight is trans-beta-cryptoxanthin, the process comprising:
  (a) mixing an oleoresin of plant material comprising xanthophylls esters with ethanol, wherein the ratio of oleoresin to ethanol is about 1:1 weight/volume;
  (b) saponifying the xanthophylls esters present in the oleoresin with potassium hydroxide without addition of water, wherein the ratio of oleoresin to potassium hydroxide is about 1:0.25 weight/weight;
  (c) applying heat to the oleoresin to elevate the temperature up to reflux at about 80-85° C.;
  (d) agitating the oleoresin for about 3 to 5 hours at about 80-85° C.;
  (e) evaporating the ethanol under vacuum followed by addition of water at about 5 times that of the oleoresin (weight/weight) to obtain a diluted resultant mixture and agitating for about 1 hour;
  (f) neutralizing the diluted resultant mixture with about 25% acetic acid to form a water layer and a precipitated xanthophylls mass;
  (g) separating the water layer from the precipitated xanthophylls mass and washing the mass with water to remove soaps and other polar soluble materials;
  (h) drying the precipitated xanthophylls mass under vacuum to obtain a crude xanthophylls mass;
  (i) washing the crude xanthophylls mass with about 1:10 hexane (weight/volume) and concentrating the hexane washings to obtain a concentrated crude xanthophylls mass;
  (j) transferring the concentrated crude xanthophylls mass to a silica gel column at a ratio of about 1:5 (weight/weight) and eluting with hexane to obtain a carotene fraction;
  (k) washing the column with about 98:2 hexane to acetone and concentrating the washings to obtain a trans-beta-cryptoxanthin-rich xanthophylls concentrate;
  (l) admixing the trans-beta-cryptoxanthin-rich xanthophylls concentrate with about 1:2 ethanol under stirring and then cooling at about 10° C. for about 8 hours;
  (m) filtering and drying the trans-beta-cryptoxanthin-rich xanthophylls concentrate under vacuum to obtain a purified trans-beta-cryptoxanthin concentrate; and
  (n) washing the purified trans-beta-cryptoxanthin concentrate with about 80:20 hexane:ethylacetate and cooling to about −10° C. for about 18 hours for precipitation to obtain high purity trans-beta-cryptoxanthin crystals.

The process by-products include beta-carotene, trans-capsanthin, zeaxanthin or mixtures thereof.

A novel feature of the present process is the preparation of high purity trans-beta-cryptoxanthin concentrate crystals from a natural source such as *capsicum* extract, which has not been reported in the art.

The following examples are given by the way of illustration of the present invention and therefore should not be construed to limit the scope of the present invention.

EXAMPLES

Example 1

A weighed quantity of 100 g of Paprika oleoresin containing 7.72% total xanthophylls and a color value of 1,23,515 units (HPLC profile of the oleoresin: beta-15.36% carotene; 10% trans-beta-cryptoxanthin; 7.6% zeaxanthin; and 31.50% trans-capsanthin) was mixed with 100 ml ethanol and 25 g potassium hydroxide pellet. The reaction mixture was heated to a temperature of 80-85° C. with stirring. This saponification process was maintained for 3-5 hours at 80-85° C. with gentle agitation. The reaction mixture was cooled, and then ethanol was distilled out from the mass. A measured volume of water (700 ml) was added to the reaction mixture and agitated for 1 hour. The solution was neutralized with 25% acetic acid solution. The water layer from the mass was separated, and the mass was washed thrice with water. The mass was collected and dried under vacuum. The saponified mass concentrate obtained was 124 g with a total xanthophylls content of 3.73% by weight (HPLC profile of the saponified mass concentrate: 22.53% beta-carotene; 12.32% trans-beta-cryptoxanthin; 11% zeaxanthin; and 29.3% trans-capsanthin).

The saponified mass concentrate was washed two times with 1:10 hexane (wt/vol) at room temperature under stirring, filtered, and the combined filtrate concentrated to obtain a concentrated crude xanthophylls mass. The concentrated crude xanthophylls mass (hexane concentrate) obtained was 72 g with a total xanthophylls content of 3.2% (HPLC profile of the concentrated crude xanthophylls mass: 39.01% beta-carotene; 21.78% trans-beta-cryptoxanthin; 5.70% zeaxanthin; and 9.86% trans-capsanthin).

The residue (saponified xanthophylls) remaining after hexane wash was 22 g, which on analysis showed a total xanthophylls content of 10% (HPLC profile of the residue: 0.7% beta-carotene; 3.43% trans-beta-cryptoxanthin; 15.32% zeaxanthin; and 52.84% trans-capsanthin).

The hexane concentrate was dissolved in a minimum amount of hexane and subjected to column chromatographic separation. The column was packed with 1:5 concentrate to Silica 100-200 mesh (wt/wt). The column was washed with hexane, and the separated band was collected and concentrated (yield 55 g with a total xanthophylls content of 2.3%, HPLC profile: 99.8% beta-carotene). The column was then eluted with 98:2 hexane:acetone (v/v), and the eluent collected and concentrated. This concentrate layer was enriched with beta-cryptoxanthin (yield 5.2 g with a total xanthophylls content of 10.26%, HPLC profile: 75.56% trans-beta-cryptoxanthin). Finally, the column was washed with acetone and the washings concentrated to obtain trans-capsanthin enriched residue.

Example 2

A quantity of approximately 100 g of Paprika oleoresin containing 6.50% total xanthophylls and a color value of 1,05,457 units (HPLC profile of the oleoresin: 15.73% beta-carotene; 9.07% trans-beta-cryptoxanthin; 10.54% zeaxanthin and 31.38% trans-capsanthin) was mixed with 100 ml ethanol and 25 g potassium hydroxide pellet. The reaction mixture was heated to a temperature of 80-85° C. with stirring. This saponification process was maintained for 3-5 hours at 80-85° C. with gentle agitation. The reaction mixture was cooled, and then ethanol was distilled out from the mass. A measured volume of water (700 ml) was added to the reaction mixture and agitated for 1 hour. The solution was neutralized with 40% acetic acid solution. The water layer from the mass was separated, and the mass was washed thrice with water. The mass was collected and dried under vacuum. The saponified mass concentrate obtained was 126 g with a total xanthophylls content of 3.73% by weight (HPLC profile of the saponified mass concentrate: 16.34% beta-carotene; 9.41% trans-beta-cryptoxanthin; 8.57% zeaxanthin; and 24.35% trans-capsanthin).

The saponified mass concentrate was washed two times with 1:10 hexane (wt/vol) at room temperature under stirring, filtered, and the combined filtrate concentrated to obtain a concentrated crude xanthophylls mass. The concentrated crude xanthophylls mass (hexane concentrate) obtained was 76.15 g with a total xanthophylls content of 3.26% (HPLC profile of the concentrated crude xanthophylls mass: 31.80% beta-carotene; 14.04% trans-beta-cryptoxanthin; 4.35% zeaxanthin; and 8.70% trans-capsanthin).

The residue (saponified xanthophylls) remaining after hexane wash was 16 g, which on analysis showed a total xanthophylls content of 11% (HPLC analysis of the residue: 1.22% beta-carotene; 0.75% trans-beta-cryptoxanthin; 33.29% zeaxanthin; and 29.99% trans-capsanthin).

The hexane concentrate was dissolved in a minimum amount of hexane and subjected to column chromatographic separation. The column was packed with 1:5 concentrate to Silica 100-200 mesh (wt/wt), eluted with hexane, and the first band separated was collected and concentrated (yield 54.72 g with a total xanthophylls content of 1.08%, HPLC profile: 85.88% beta-carotene). The column was then eluted with 98:2 hexane:acetone (v/v) collecting the eluent fraction and concentrated. This fraction was enriched with beta-cryptoxanthin, yielding 4.02 g with a total xanthophylls content of 9% (HPLC profile of the enriched beta-cryptoxanthin concentrate: 76.04% trans-beta-cryptoxanthin). Finally the column was washed with acetone.

The 4.02 g fraction concentrate was stirred with 1:2 ethanol (wt/vol) for 1 hr, chilled for 8 hrs at 10° C., filtered, and the precipitate dried under vacuum. The yield obtained was 0.42 g crystalline precipitate with a total xanthophylls content of 42.45%. The HPLC profile of the crystalline precipitate showed 98.3% trans-beta-cryptoxanthin.

Example 3

A weighed quantity of Paprika oleoresin (100 g) containing 6-8% by weight total xanthophylls and a color value of 1,00,000 units (HPLC profile of the oleoresin: 15.36% beta-carotene; 10% trans-beta-cryptoxanthin; 7.6% zeaxanthin; and 31.50% trans-capsanthin) was mixed with 100 ml ethanol and 25 g potassium hydroxide pellet. The reaction mixture was heated to a temperature of 80-85° C. with stirring. This saponification process was maintained for 3-5 hours at 80-85° C. with gentle agitation. The reaction mixture was cooled and then ethanol was distilled off from the mass under vacuum. A measured volume of water (700 ml) was added to the reaction mixture and agitated for 1 hour. The solution was neutralized with 25% acetic acid solution. The water layer from the mass was removed, and the mass was washed thrice with water. The mass was collected and dried under vacuum. The saponified mass concentrate obtained was 121.75 g with a total xanthophylls content of 4.92% by wt (HPLC profile of the saponified mass concentrate: 21.76% beta-carotene; 12.74% trans-beta-cryptoxanthin; 10.13% zeaxanthin; and 38.25% trans-capsanthin).

The saponified mass concentrate was washed two times with 1:10 hexane (wt/vol) at room temperature under stirring, filtered, and the combined filtrate concentrated to get a concentrated crude xanthophylls mass. The concentrated crude xanthophylls mass (hexane concentrate) obtained was 85.81 g with a total xanthophylls content of 3.21% by wt (HPLC profile of the concentrated crude xanthophylls mass:

35.28% beta-carotene; 19.65% trans-beta-cryptoxanthin; 3.99% zeaxanthin; and 13.88% trans-capsanthin).

The residue (saponified xanthophylls) remaining after hexane wash was 25.65 g, which on analysis showed a total xanthophylls content of 10.42% by wt (HPLC analysis of the residue: 0.7% beta-carotene; 1.24% trans-beta-cryptoxanthin; 18.98% zeaxanthin; and 52.32% trans-capsanthin.

The hexane concentrate was dissolved in minimum amount of hexane and subjected to column chromatographic separation. The column was packed with 1:5 concentrate to Silica gel 100-200 mesh (wt/wt), eluted with 5-8 volumes of hexane, and the first band separated was eluted and concentrated (yield 55 g with a total xanthophylls content of 2.29% wt, HPLC profile: 99% beta-carotene). The column was then eluted with 98:2 hexane:acetone (vol/vol) collecting the eluent fraction and concentrated. This concentrate was enriched with beta-cryptoxanthin, yielding 9.06 g with a total xanthophylls content of 6.12% by wt (HPLC profile of the enriched beta-cryptoxanthin concentrate: 71.80% trans-beta-cryptoxanthin). Finally the column was eluted with acetone.

The 9.06 g beta-cryptoxanthin concentrate was stirred with 1:2 ethanol (wt/vol) for 1 hr, chilled for 8 hours at 10° C., filtered, and the precipitate dried under vacuum. The yield obtained was 0.5 g with a total xanthophylls content of 42.35% by wt. The HPLC profile of the crystal showed 98.3% trans-beta-cryptoxanthin content.

The 0.5 g beta-cryptoxanthin precipitate was dissolved in a minimum amount of 80:20 hexane:ethylacetate (vol/vol) and chilled for 18 hrs at −10° C., filtered, and the precipitate dried under vacuum. The yield obtained was 0.03 g with a total xanthophylls content of 80% and HPLC profile for trans-beta-cryptoxanthin of 98.50%.

Example 4

Anti-Resorptive Property of β-Cryptoxanthin and its Effect on Bone Mechanical Strength Description of Test Materials:

| Samples | Total Xanthophyll content | Source |
| --- | --- | --- |
| BCX-A | 80.3% | Obtained through Marigold oleoresin |
| BCX-B | 0.793% | Obtained through Orange fruits |
| BCX-C | 10%* | Obtained through Paprika oleoresin |

*For experimental purpose the sample was diluted to 1%.

Test System:

Wistar rats of age between 8 to 10 weeks and weighing between 180-230 gm.

Housing of Animals:

Animals were divided into 5 groups of 6 animals in each group. Each cage was labeled with the name of group, protocol number, species/strain and sex of animal. The total number of cages used was 10 for 30 animals. Each cage housed three animals at the temperature (25° C.±2) and 50-70% relative humidity with 12 h light/dark cycle. All the animals had free access to water. Rice husk was used as bedding in the cages. The cages were cleaned on daily basis.

Bilateral Ovariectomy Procedure:

All surgical instruments were sterilized before use. The dorsal skin of rat was shaved and disinfected using Povidone iodine solution. Ovariectomy was performed by two dorsolateral incisions, approximately 1 cm long above the ovaries. With the use of a sharp dissecting scissors, skin cut was made almost together with the dorsal muscles to access peritoneal cavity. The ovary was found surrounded by a variable amount of fat. Blood vessels were ligated to prevent blood loss. The connection between the fallopian tube and the uterine horn was cut and the ovary was moved out and three single catgut stitches were placed on the skin.

Grouping:

| GROUP | TREATMENT | Dose | No. of Animals |
| --- | --- | --- | --- |
| Group-1 | Sham Control (Corn oil) | 0.5 ml/100 g | 6 |
| Group-2 | Ovariectomized control (OVX control) | — | 6 |
| Group-3 | OVX + β Cryptoxanthin (BCX-A) | 20 μg/100 g | 6 |
| Group-4 | OVX + β Cryptoxanthin (BCX-B) | 20 μg/100 g | 6 |
| Group-5 | OVX + β Cryptoxanthin (BCX-C) | 20 μg/100 g | 6 |

Study Procedure:

Rats from Group 1 were operated for sham surgery under Ketamine (70 mg/kg)+Xylazine (10 mg/kg) (intra peritoneal) anesthesia. Rats from Groups 2, 3, 4 and 5 were operated for bilateral ovariectomy (OVX) under Ketamine+Xylazine (i.p.) anesthesia. The OVX-operated animals were fed with standard commercial laboratory chow amounts matched with the Sham operated group. The operated animals were housed individually and were allowed to recover for 2 weeks.

Test compounds were dissolved in corn oil. Concentrations of 20 μg/100 g of body weights were administered orally to rats in respective groups through oral gavage needle once daily for 3 weeks. Control rats received corn oil (0.5 ml/100 g of body weight) orally.

On last day of treatment, urine samples were collected by micturation induced by manual pressure from overnight fasted animals and preserved at −20° C. till further analysis.

Statistical Analysis:

All results were analyzed using One Way ANOVA followed by Dunnett's multiple comparison test. Considering confidence interval of $P<0.05$.

Estimation of Bone Collagen Metabolite (Pyridinoline Crosslinks) in Urine:

Pyridinoline Crosslinks are the bone collagen metabolites which appear in urine when the bone resorption process is accelerated and is considered as an early important marker of osteoporosis.

OVX control animals showed significant increase in Pyridinoline Crosslinks in urine which confirms the successful induction of osteoporosis after ovariectomy procedure. BCX-C treatment moderately reduced the urinary excretion of Pyridinoline Crosslinks to a considerable extent, as did BCX-A and BCX-B, as shown below in Table No. 1. This confirms the therapeutic utility of BCX treatment in estrogen deficiency related osteoporosis.

TABLE NO. 1

Pyridinoline Crosslinks Determination
Pyridinoline Crosslinks (nmol/mmol of Creatinine)

| Sham Control | OVX control | BCX-A | BCX-B | BCX-C |
| --- | --- | --- | --- | --- |
| 17.15 | 17.64 | 6.71 | 10.27 | 14.48 |
| 1.89 | 21.69 | 9.80 | 9.64 | 15.64 |
| 29.71 | 22.31 | 10.52 | 10.04 | 16.87 |
| 33.50 | 14.68 | 12.15 | 10.80 | 10.26 |

TABLE NO. 1-continued

Pyridinoline Crosslinks Determination
Pyridinoline Crosslinks (nmol/mmol of Creatinine)

| Sham Control | OVX control | BCX-A | BCX-B | BCX-C |
|---|---|---|---|---|
| 4.40 | 14.79 | 34.37 | 24.17 | 13.77 |
| 1.50 | 13.97 | 12.19 | 23.12 | 24.62 |
| Mean = 14.69 | 17.51 | 14.29 | 14.68 | 15.94 |

Determination of Bone (Femur) Density:

Cessation of the ovarian function in humans leads to increase in bone turnover, a negative bone balance, and a net decrease in bone density; these changes are also evident in surgically ovariectomized rats.

A significant OVX induced decrease in bone density was observed in Group 2. BCX-A, BCX-B and BCX-C treatment prevented OVX associated decrease in bone density. BCX-C showed better activity than BCX-A and BCX-B in preventing OVX induced loss of bone density as shown below in Table No. 2.

TABLE NO. 2

Bone Density Determination
Bone Density (g/cm3)

| Sham Control | OVX control | BCX-A | BCX-B | BCX-C |
|---|---|---|---|---|
| 1.253 | 1.121 | 1.173 | 1.1858 | 1.1902 |
| 1.186 | 1.131 | 1.178 | 1.0669 | 1.2437 |
| 1.169 | 1.167 | 1.175 | 1.1785 | 1.2065 |
| 1.208 | 1.131 | 1.186 | 1.1893 | 1.1593 |
| 1.230 | 1.162 | 1.141 | 1.0782 | 1.1965 |
| 1.205 | 1.130 | 1.171 | 1.2490 | 1.1978 |
| Mean ± SD = 1.209 ± 0.030 | 1.140 ± 0.019 | 1.171 ± 0.015 | 1.157 ± 0.070 | 1.198 ± 0.027 |

The results obtained from the above experiments confirm that beta-cryptoxanthin obtained from Paprika source (BCX-C) shows better anti-resorptive property than beta-cryptoxanthin obtained from Marigold and Orange source.

Determination of Ultimate Failure Load of Bones (Tibiae):

Bone fragility can be defined broadly as the susceptibility to fracture. One function of bones is to carry loads. Fractures occur when loads exceed the bone strength, so weakened bones should be considered fragile. During traumatic loading, such as falling on the ground, fracture will occur if the energy from the fall exceeds the mechanical energy that the bone can absorb. Osteoporotic bones absorb very little energy before breaking (failure load) and are therefore more susceptible to fracture resulting from trauma. In this study, the failure load was measured using Three Point Bending test.

In ovariectomized animals there was significant decrease in maximal load values for tibial mid shaft indicating the significant loss of cancellous bone. From the results given below in Table No. 3 it is evident that, BCX-C treatment significantly prevented the loss of mechanical strength of cancellous bone.

TABLE NO. 3

Determination of Failure Load of Bone
Failure load (N)

| Sham Control | OVX control | BCX-A | BCX-B | BCX-C |
|---|---|---|---|---|
| 77.14 | 45.47 | 51.9 | 59.63 | 66.66 |
| 69.89 | 43.22 | 65.25 | 56.91 | 57.00 |
| 58.33 | 54.11 | 53.41 | 59.77 | 65.72 |
| 61.22 | 45.63 | 49.71 | 62.38 | 54.31 |
| 58.33 | 42 | 73.71 | 75.23 | 65.66 |
| 55.76 | 45.62 | 63.28 | 57.65 | 48.90 |
| Mean ± SD = 63.445 ± 8.31 | 46.00 ± 4.24 | 59.54 ± 9.38 | 61.92 ± 6.79 | 59.70 ± 7.39 |

Figure 2:
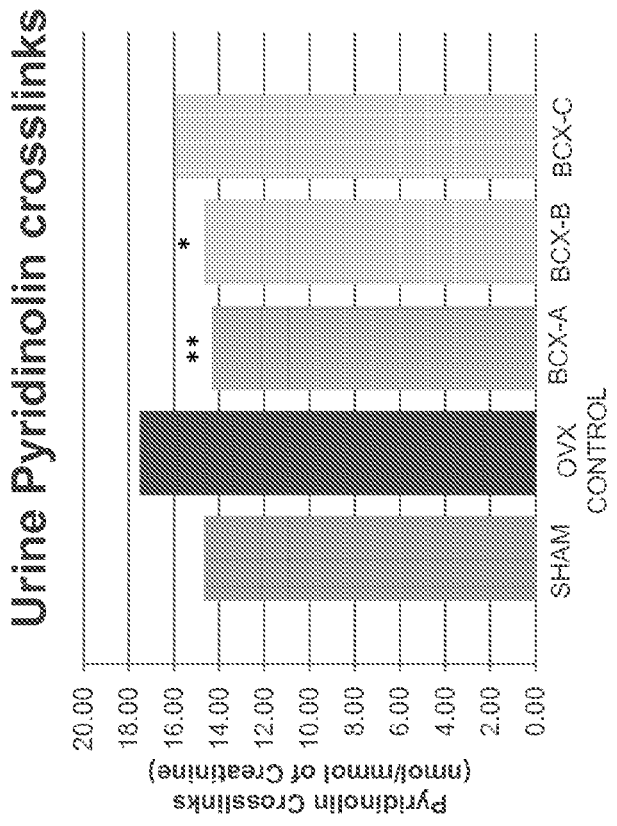
FIG. 2 is a graph that depicts the Pyridinoline Crosslinks determination in the sham control, OVX control, and BCX-A, -B, and -C groups.
Figure 3:
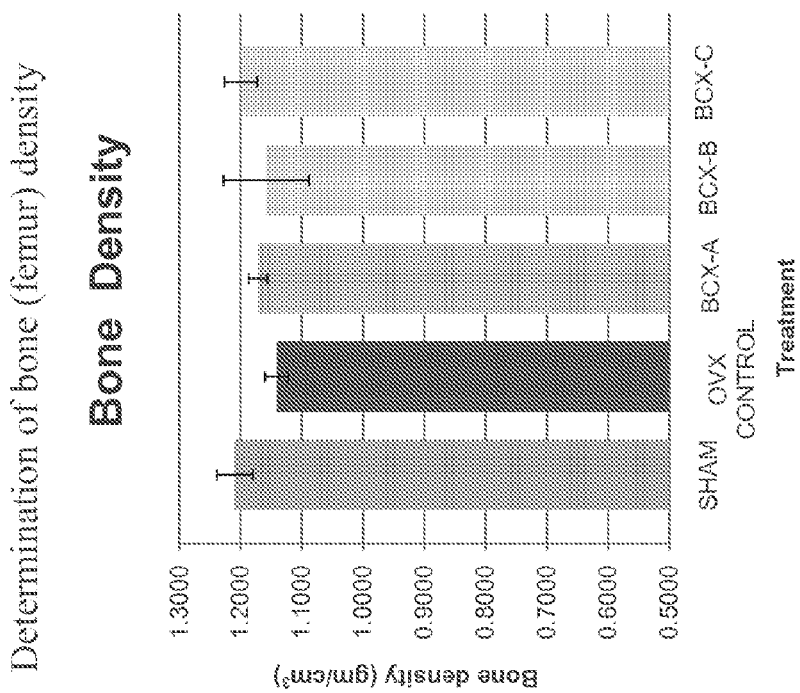
FIG. 3 is a graph that depicts the bone density determination in the sham control, OVX control, and BCX-A, -B, and -C groups.
Figure 4:
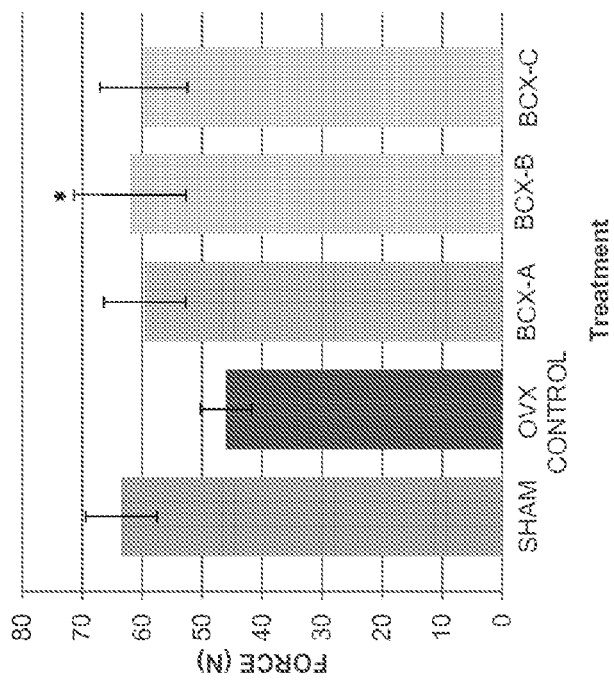
FIG. 4 is a graph that depicts the failure load of bone in the sham control, OVX control, and BCX-A, -B, and -C groups.

The data represented in Tables No. 1, 2 and 3 are plotted in FIGS. 2, 3, and 4, respectively, as shown in the drawings accompanied with the specification.

CONCLUSION

Trans-beta-cryptoxanthin possesses significant anti-osteoporotic activity in an OVX rat model. BCX-C (Paprika source) significantly improved mass and mechanical strength of bones in ovariectomized rats compared to BCX-A (Marigold source) & B (Orange source).

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A process for the preparation of a trans-beta-cryptoxanthin enriched concentrate from plant material comprising about 10-80% by weight total xanthophylls, of which about 75-98% by weight is trans-beta-cryptoxanthin, the process comprising:
   (a) mixing an oleoresin of plant material comprising xanthophylls esters with an aliphatic alcoholic solvent;
   (b) saponifying the xanthophylls esters present in the oleoresin with an alkali at an elevated temperature;
   (c) removing the aliphatic alcoholic solvent followed by addition of water to obtain a diluted resultant mixture;
   (d) adding a diluted organic acid to the diluted resultant mixture to form a water layer and a precipitated xanthophylls mass;
   (e) removing the water layer and washing the precipitated xanthophylls mass with a polar solvent;
   (f) drying the precipitated xanthophylls mass to obtain a crude xanthophylls mass;
   (g) washing the crude xanthophylls mass with a non-polar solvent and concentrating the non-polar solvent washings to obtain a concentrated crude xanthophylls mass;

(h) transferring the concentrated crude xanthophylls mass to a silica gel column and washing with a non-polar solvent;

(i) eluting the column with a mixture of non-polar and polar solvent and concentrating the elutions to obtain a trans-beta-cryptoxanthin-rich xanthophylls concentrate;

(j) admixing the trans-beta-cryptoxanthin-rich xanthophylls concentrate with an aliphatic alcohol and then cooling; and (k) filtering and drying the trans-beta-cryptoxanthin-rich xanthophylls concentrate to obtain the purified trans-beta-cryptoxanthin concentrate.

2. The process of claim 1, wherein the xanthophylls esters in the oleoresin of plant material in step (a) are present at about 6-8% by weight.

3. The process of claim 1, wherein the ratio of oleoresin to alcohol in step (a) ranges from about 1:0.25 to about 1:1 weight/volume.

4. The process of claim 1, wherein the ratio of oleoresin to alkali in step (b) ranges from about 1:0.25 to 1:0.5 weight/weight.

5. The process of claim 1, wherein the diluted organic acid of step (d) is acetic acid or phosphoric acid.

6. The process of claim 1, wherein the polar solvent of step (e) is water.

7. The process of claim 1, wherein a carotene concentrate is obtained by distilling the non-polar solvent washing of step (h).

8. The process of claim 1, wherein the non-polar solvent and polar solvent of step (i) are in a ratio of about 95:5 to about 98:2.

9. The process of claim 1, wherein the trans-beta-cryptoxanthin-rich xanthophylls concentrate of step (i) comprises at least about 10% by weight of total xanthophylls, of which trans-beta-cryptoxanthin content is at least about 75% by weight.

10. The process of claim 1, wherein the purified trans-beta-cryptoxanthin concentrate of step (k) comprises at least about 40% by weight of total xanthophylls, of which trans-beta-cryptoxanthin content is at least about 90% by weight.

11. The process of claim 1, further comprising a step (l): washing the purified trans-beta-cryptoxanthin concentrate with a mixture of non-polar and ester solvent and cooling for precipitation to obtain high purity trans-beta-cryptoxanthin crystals.

12. The process of claim 11, wherein the high purity trans-beta-cryptoxanthin crystals of step (l) comprises at least about 80% by weight of total xanthophylls, of which trans-beta-cryptoxanthin content is at least about 98% by weight.

13. The process of claim 11, wherein the non-polar solvent and ester solvent of step (l) are in a ratio of about 80:20 to about 90:10.

14. The process of claim 11, wherein the cooling in step (l) is performed at temperature of about $-10°$ C.

15. The process of claim 1, wherein the total xanthophylls comprise byproducts selected from zeaxanthin, trans-capsanthin, beta-carotene, trace amounts of other carotenoids, and any combinations thereof.

16. The process of claim 1, wherein the plant material is selected from the group consisting of fruits, vegetables, and mixtures thereof.

17. The process of claim 16, wherein the plant material is from a *capsicum*.

18. The process of claim 1, wherein the aliphatic alcohol of step (a) or (j) is selected from the group consisting of ethanol, methanol, isopropyl alcohol, and mixtures thereof.

19. The process of claim 1, wherein the alkali of step (b) is selected from the group consisting of sodium hydroxide, potassium hydroxide, and mixtures thereof.

* * * * *

UNITED STATES PATENT AND TRADEMARK OFFICE
CERTIFICATE OF CORRECTION

PATENT NO. : 9,771,323 B2  
APPLICATION NO. : 14/763470  
DATED : September 26, 2017  
INVENTOR(S) : Sunilkumar et al.

Page 1 of 1

It is certified that error appears in the above-identified patent and that said Letters Patent is hereby corrected as shown below:

On the Title Page

In the inventors item (72), "Madapura Lingappiah Shankaranarayana" should appear as --Madapura Lingappiah Shankaranarayana, DECEASED--.

Signed and Sealed this
First Day of May, 2018

Andrei Iancu
*Director of the United States Patent and Trademark Office*